(12) United States Patent
Bozzano

(10) Patent No.: US 8,022,002 B2
(45) Date of Patent: Sep. 20, 2011

(54) INTEGRATED REGENERATION OF NON-NOBLE METAL CATALYSTS

(75) Inventor: Andrea G. Bozzano, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 100 days.

(21) Appl. No.: 12/410,015

(22) Filed: Mar. 24, 2009

(65) Prior Publication Data

US 2010/0248943 A1    Sep. 30, 2010

(51) Int. Cl.
*B01J 38/34* (2006.01)
(52) U.S. Cl. .......................................... 502/43
(58) Field of Classification Search .......................... None
See application file for complete search history.

(56) References Cited

U.S. PATENT DOCUMENTS

| | | | |
|---|---|---|---|
| 4,341,623 A * | 7/1982 | Bertolacini et al. | 208/113 |
| 4,550,217 A * | 10/1985 | Graziani et al. | 585/324 |
| 4,935,568 A | 6/1990 | Harandi et al. | 585/300 |
| 5,002,915 A * | 3/1991 | Harandi et al. | 502/51 |
| 5,827,793 A * | 10/1998 | Hu | 502/41 |
| 7,053,260 B2 | 5/2006 | Xu et al. | 585/638 |
| 7,115,791 B2 | 10/2006 | Kabin et al. | 585/640 |
| 7,332,134 B2 | 2/2008 | Lattner | 422/145 |
| 7,402,720 B2 | 7/2008 | Van Egmond | 585/802 |
| 7,404,891 B2 | 7/2008 | Van Egmond et al. | 208/159 |
| 7,439,414 B2 | 10/2008 | Miller et al. | 585/640 |
| 7,816,294 B2 * | 10/2010 | Chu | 502/42 |
| 2007/0037692 A1 | 2/2007 | Beech, Jr. et al. | 502/56 |

FOREIGN PATENT DOCUMENTS

| WO | WO 2004018092 A1 * | 3/2004 |
|---|---|---|
| WO | WO2008039552 | 4/2008 |
| WO | WO2008110530 | 9/2008 |

* cited by examiner

*Primary Examiner* — Melvin Mayes
*Assistant Examiner* — Stefanie Cohen
(74) *Attorney, Agent, or Firm* — Arthur E Gooding

(57) ABSTRACT

Regeneration flue gas streams containing unacceptable levels of CO can be effectively combusted (i.e., for more complete combustion or oxidation of CO to $CO_2$) by contact with a second catalyst undergoing regeneration, for example in a second regenerator. While the second catalyst may also be regenerated by contact with an oxygen-containing gas stream, this second catalyst additionally comprises a noble metal, or is present in combination with a combustion comprising a noble metal. Representative catalysts used in an integrated regeneration process are those used for oxygenate conversion and olefin cracking, both for the purpose of producing light olefins (e.g., ethylene and propylene).

20 Claims, 2 Drawing Sheets

INTEGRATED REGENERATION OF NON-NOBLE METAL CATALYSTS

FIELD OF THE INVENTION

The invention relates to the regeneration of non-noble metal catalysts in which a resulting flue gas containing carbon monoxide is introduced into a second regenerator containing a combustion promoter comprising a noble metal catalyst that combusts at least some of the carbon monoxide to carbon dioxide. A representative non-noble metal catalyst is for cracking $C_4$-$C_7$ olefins, with the flue gas stream from the regeneration of this catalyst being contacted with a catalyst for converting oxygenates to light olefins.

DESCRIPTION OF RELATED ART

Catalytic processes for the conversion of hydrocarbons are well known and extensively used. Invariably the catalysts used in these processes become deactivated, most commonly due to the deposition coke, or hydrocarbonaceous solids having a high carbon to hydrogen ratio, and/or other poisons on the catalyst surface. Regeneration or reconditioning of the catalyst to remove coke deposits in many cases can restore the activity of the catalyst. Regeneration is commonly carried out by contacting the spent or coke-containing catalyst at high temperature with an oxygen-containing gas to combust and thereby remove the coke. Catalyst coke burning processes can be carried out in situ by maintaining the catalyst (e.g., as a fixed bed), in the same reaction vessel used for its normal reaction or conversion. A swing-bed system, for example, allows the ability to alternate two or more catalyst beds in separate reactors between reaction zone and regeneration zone environments. In this manner, one catalyst loading is continually maintained "on-line" while another is being regenerated.

Other regenerations involve removing catalyst from the reaction vessel and transporting it to a separate regenerator for coke removal. The semi-continuous or continuous transfer of spent catalyst particles from a reaction zone to a regeneration zone for coke removal, and the return of regenerated catalyst back to the reaction zone, are commonly practiced in the art. Catalysts used in fluidized bed processes, for example, are often regenerated continuously due to the fast rate of coke deposition. A well-known example of such a process, involving the continual cycling of catalyst between a reactor and a regenerator, is fluid catalytic cracking (FCC).

Whether performed in situ, or in a semi-continuous or continuous manner, catalyst regeneration requires burning coke deposits from the catalyst by adding air or other oxygen-containing gas to a regeneration zone. This zone may be either in the reactor used for the normal reaction or conversion process (for in situ regeneration) of the catalyst or in a separate regenerator. The burning of the hydrocarbonaceous coke with oxygen normally results in a mixture of carbon monoxide (CO) and carbon dioxide ($CO_2$) that exits in a flue gas stream from regeneration. Environmental concerns favor the complete combustion of CO to $CO_2$, and in many locations, the discharge of CO-containing gases is not even permitted. The desire for complete combustion, however, is complicated by the considerable oxidation of CO to $CO_2$ that usually occurs in an upper portion of the regenerator where no catalyst is available to act as a heat sink. This phenomenon, known as "afterburning," results in extremely high temperatures that can damage the regenerator and associated equipment.

A possibility for achieving complete CO combustion in the catalyst regenerator without excessive reactor temperatures involves the use of a CO-burning promoter or combustion promoter. A typical combustion promoter is mixed with catalyst being regenerated in the regenerator. In the case of catalyst being regenerated in a fluidized state, for example, the combustion promoter is often in the form of a fluidizable solid catalyst containing trace amounts, in the parts per million range, of a noble metal such as platinum. Alternatively, small quantities of this catalytically active metal may be incorporated into the catalyst itself, for example, during manufacture or by the addition of a liquid solution containing the metal to the regenerator.

The use of a combustion promoter containing a noble metal, however, is not a satisfactory solution for achieving complete combustion of deposited coke in all catalyst regeneration applications. In particular, the noble metal that effectively catalyzes oxidation (combustion) in the regeneration zone may be unfavorable in the overall reaction or conversion process when in the reaction zone. For example, the addition of platinum or other noble metal to some types of reactions may reduce product yields by catalyzing byproduct formation reactions and/or reducing the activity of active sites for catalyzing desired reactions. A representative conversion process that does not utilize a noble metal catalyst, and in which the introduction of a noble metal function (e.g., by the addition of a conventional combustion promoter) would be detrimental is an olefin cracking process. The integration of such a process, namely for cracking of $C_4$-$C_7$ olefins, with an oxygenate conversion process, both of which processes produce light weight olefins (e.g., ethylene and propylene) is described, for example, in U.S. Pat. No. 7,317,133.

There exists a need in the art for methods for the effective regeneration of catalysts that do not contain a noble metal, and especially methods in which CO emissions in regeneration flue gas streams is minimized or eliminated.

SUMMARY OF THE INVENTION

The present invention is associated with the discovery that regeneration flue gas streams containing unacceptable levels of CO can be effectively combusted (i.e., for more complete combustion or oxidation of CO to $CO_2$) by contact with a second catalyst undergoing regeneration, for example in a second regenerator. While the second catalyst may also be regenerated by contact with an oxygen-containing gas stream, this second catalyst additionally comprises a noble metal, or is present in combination with a combustion promoter comprising a noble metal. In contrast, the catalyst that is regenerated to provide the CO-containing regeneration flue gas stream is generally a non-noble metal catalyst (i.e., does not comprise a noble metal) and is not combined with a noble metal combustion promoter, possibly due to the adverse effect of a noble metal on the performance (i.e., activity and/or selectivity) of this catalyst for a particular reaction or conversion process (e.g., a hydrocarbon conversion process such as olefin cracking).

Embodiments of the invention are therefore directed to methods for regenerating a catalyst having coke deposited thereon, generally due to coke buildup during the course of the normal reaction environment of the catalyst. The methods comprise contacting an oxygen-containing regeneration gas stream (e.g., air or nitrogen-enriched air) with the catalyst to burn at least a portion of the coke, thereby restoring some or all of the activity of the catalyst lost through the coke deposition. Contact with the oxygen-containing gas stream provides a regeneration flue gas comprising the incomplete combustion product CO, often in amounts such that release of this flue gas into the atmosphere is environmentally unfavorable and/or impermissible in view of local regulations. To overcome this problem, all or at least a portion of this regeneration flue gas is contacted with a second catalyst, which is normally also being regenerated (e.g., all or a portion of the second catalyst has coke deposited thereon), for example by contact with a separate, second oxygen-containing gas. The second catalyst, however, comprises a noble metal or is admixed with a combustion promoter comprising a noble metal, to combust at least a portion of the CO introduced with the regeneration flue gas. This more complete combustion through contact with the second catalyst can therefore convert some or all of the CO to $CO_2$, such that a second regeneration flue gas stream, provided by contacting of the second catalyst with the regeneration flue gas comprising CO, has, for example CO in a representative amount of less than about 1% by volume.

Additional embodiments of the invention are directed to integrated processes for regenerating a catalyst. The processes comprise feeding an oxygen-containing regeneration gas stream to a regenerator containing a non-noble metal catalyst to burn all or at least a portion of coke deposited on this catalyst. A regeneration flue gas stream comprising CO is removed from this regenerator. At least a portion of this regeneration flue gas stream, as well as a second oxygen-containing regeneration gas stream, are fed to a second regenerator containing a second catalyst comprising a noble metal, or admixed with a combustion promoter comprising a noble metal. The presence of this noble metal provides a catalytically active agent, in the second catalyst or combustion promoter, for the combustion of at least a portion of the CO to $CO_2$, thereby minimizing or even eliminating the overall CO emissions (e.g., in a second regeneration flue gas stream removed from the second regenerator) in the integrated process, to the environment.

Advantageously, the addition of the regeneration flue gas stream to the second regenerator can be varied, depending on a number of considerations including those related to the flue gas quality, such as the content of water and/or other impurities that may be detrimental to the second catalyst (e.g., due to limited hydrothermal stability) in its regeneration environment. According to a particular embodiment, at least a portion of the regeneration flue gas stream to the second regenerator is fed as a mixture, with a second oxygen-containing regeneration gas stream used to regenerate the second catalyst, to an inlet of the second regenerator, for example at a bottom section. Alternatively, the regeneration flue gas stream may be fed or introduced to alternate locations of the second regenerator or associated equipment. Shorter residence times and/or cooler contacting temperatures between the second catalyst and the CO-containing regeneration flue gas stream, for example to reduce the potential for causing hydrothermal destabilization, may be obtained by introducing the CO-containing regeneration flue gas stream to a catalyst cooler section of the second regenerator. Otherwise, this regeneration flue gas may be introduced to an upper portion of the second regenerator, possibly into an upper dense bed section of catalyst in the second regenerator or even above this bed, such as in a top section. Important considerations are sufficient residence time, temperature, and contact with the noble metal (in the second catalyst and/or combustion promoter) to effectively combust the CO in the regeneration flue gas.

In particular embodiments of the integrated catalyst regeneration processes described above, a regenerated non-noble metal catalyst and/or a regenerated second catalyst (both of which, for example, comprise less than about 3% by weight of deposited coke after regeneration) are removed from the regenerator and second regenerator, respectively. The regenerated catalysts may then be returned to their respective reaction zones (or reaction environments) for carrying out the conversion processes for which the catalysts are used in their normal services. An integrated process of commercial interest is the regeneration of a non-noble metal catalyst that, in its normal service, is contacted with a feed stream comprising $C_4$-$C_7$ olefins that are cracked to lighter olefins in an olefin cracking reaction zone, particularly ethylene and propylene. The second catalyst may, in its normal service, be contacted with a feed stream comprising an oxygenate (e.g., methanol) that is also converted to these lighter olefins in an oxygenate conversion reaction zone, with the $C_4$-$C_7$ olefins obtained as byproducts.

Further embodiments of the invention are directed to integrated catalyst regeneration processes comprising (i) combusting coke deposited on a catalyst in a first regenerator, wherein the catalyst does not comprise a noble metal and is not admixed with a combustion promoter comprising a noble metal, to provide a regeneration flue gas stream comprising CO and (ii) flowing the regeneration flue gas stream to a second catalyst in a second regenerator, wherein the second catalyst comprises a noble metal or is admixed with a combustion promoter comprising a noble metal. In particular embodiments, the catalyst regenerated in step (i) is used in a process for cracking $C_4$-$C_7$ olefins to ethylene and propylene and/or the second catalyst regenerated in step (ii) is used in a process for the conversion of methanol to light olefins, with the production of the $C_4$-$C_7$ olefins as byproducts.

Still further embodiments of the invention are directed to processes for cracking $C_4$-$C_7$ olefins to ethylene and propylene in the presence of a non-noble metal catalyst and regenerating this catalyst by contacting it with an oxygen-containing regeneration gas stream to burn at least a portion of the coke deposited on the catalyst and provide a regeneration flue gas stream comprising carbon monoxide (CO). During this regeneration, the non-noble metal catalyst useful for cracking $C_4$-$C_7$ olefins is not combined or mixed with a combustion promoter comprising a noble metal. At least a portion of the regeneration flue gas stream is contacted with a second catalyst comprising a noble metal, or admixed with a combustion promoter comprising a noble metal, to combust at least a portion of the CO, while the second catalyst is also being regenerated by contact with a second oxygen-containing regeneration gas stream.

Yet further embodiments of the invention are directed to processes for the conversion of oxygenates such as methanol to light olefins such as ethylene and propylene in the presence of a catalyst and regenerating this catalyst by contacting it with a regeneration flue gas stream comprising CO provided by the regeneration of a different, non-noble metal catalyst in the presence of an oxygen-containing regeneration gas stream. The regeneration of the catalyst used in the oxygenate conversion process (e.g., methanol-to-light olefins process) is carried out by contacting this catalyst, having coke deposited thereon, with (in addition to the regeneration flue gas stream comprising CO) a second oxygen-containing gas stream, which may be separate from, or the same as, the oxygen-containing gas stream used to regenerate the non-noble metal catalyst. This catalyst used in the oxygenate conversion process comprises a noble metal or is admixed (e.g., during its regeneration) with a combustion promoter comprising a noble metal (e.g., platinum). In a particular embodiment, the non-noble metal catalyst is used for cracking $C_4$-$C_7$ olefins, and possibly those produced as byproducts in the oxygenate conversion process.

These and other aspects and embodiments associated with the present invention are apparent from the following Detailed Description.

Figure 1:
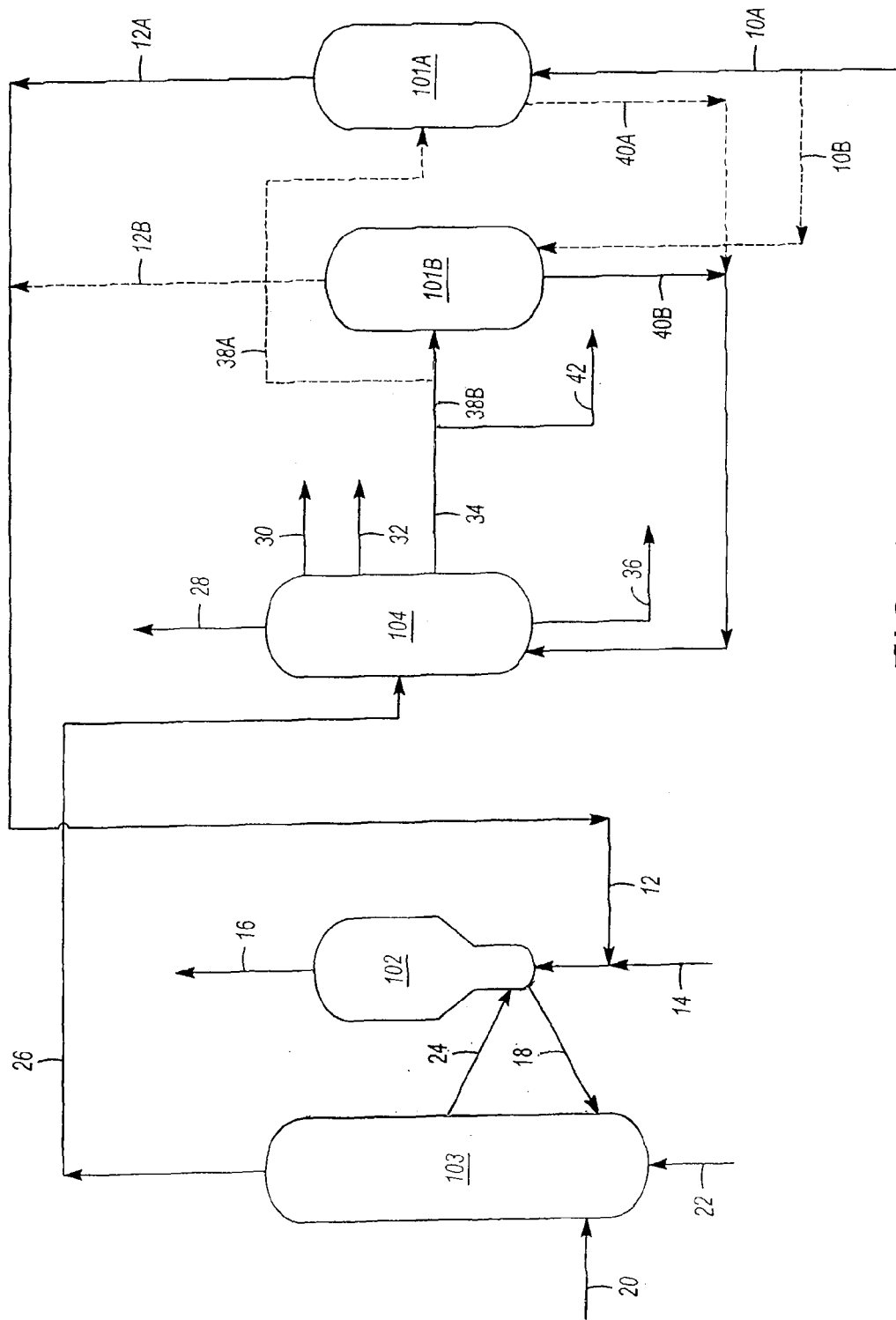
FIG. 1 depicts a representative, integrated process for producing light olefins such as ethylene and propylene through oxygenate conversion and olefin cracking.

The same reference numbers are used to illustrate the same or similar features throughout the drawings. The drawings are to be understood to present an illustration of the invention and/or principles involved. As is readily apparent to one of skill in the art having knowledge of the present disclosure, catalyst regeneration processes, and particularly those involving the regeneration of catalysts in separate regenerators in which one regenerator contains a non-noble metal catalyst that is not admixed with a combustion promoter comprising a noble metal and another regenerator contains a catalyst that comprises a noble metal or is admixed with a combustion promoter comprising a noble metal, according to various other embodiments of the invention, will have configurations and components determined, in part, by their specific use.

DETAILED DESCRIPTION

The present invention is associated with the discovery of integrated catalyst regeneration processes that emit overall reduced quantities of carbon monoxide (CO) by combusting it more completely to carbon dioxide ($CO_2$) through the integration of regenerations of at least two catalysts. According to one method, a catalyst having deposited coke is contacted with an oxygen-containing regeneration gas stream to burn at least a portion of the coke and provide a regeneration flue gas stream. The regeneration flue gas stream contains CO, at least a portion of which is beneficially combusted to $CO_2$ by contacting some or all of the regeneration flue gas with a second catalyst (or feeding at least a portion of the regeneration flue gas to a second regenerator containing the second catalyst). Representative amounts of CO in the regeneration flue gas stream, prior to its introduction into a second regenerator in which the second catalyst and optionally a combustion promoter are disposed, can range generally from about 5% to about 65%, typically from about 10% to about 50%, and often from about 15% to about 35% by volume (or as measured in the gas stream on a molar basis).

The presence of CO in this regeneration flue gas stream is often the result of a lack of a noble metal in the catalyst being regenerated or the lack a combustion promoter comprising a noble metal. The addition of a noble metal to the reaction environment of some catalysts may be detrimental to the conversion to, and/or selectivity for, the desired reaction products, for example the light olefins ethylene and propylene.

The CO-containing regeneration flue gas stream preferably contains only limited amounts of impurities that can adversely affect the performance of the second catalyst, especially when contacted with the second catalyst under the high temperatures associated with regeneration. These impurities can include water if the second catalyst is susceptible to hydrothermal deactivation. According to representative embodiments, therefore, the regeneration flue gas stream has a water content of generally less than about 3%, typically less than about 1%, and often less than about 0.1%, by volume.

Because the second catalyst comprises a noble metal and/or is admixed with a combustion promoter comprising a noble metal, the regeneration environment of this catalyst is favorable for the more complete, catalytic combustion of CO to $CO_2$. Therefore, a second regeneration flue gas stream, provided by contacting some or all of the regeneration flue gas with a second catalyst, as discussed above, can be released to the environment, normally without concern for CO contamination. According to various embodiments of the invention, the second regeneration flue gas stream will comprise CO generally in an amount of less than about 10%, typically less than about 5%, and often less than about 1%, by volume.

One or more noble metals are therefore present in the regeneration environment of the second catalyst, either deposited on the second catalyst itself, or otherwise included in the regeneration environment as a combustion promoter, for example as solid material having the noble metal disposed thereon. In some cases, a liquid solution of the noble metal may be introduced into the regeneration environment, thereby impregnating the second catalyst with the noble metal. Noble metals include platinum, palladium, rhodium, ruthenium, gold, osmium, and iridium, with platinum being preferred for the catalytic combustion of CO to $CO_2$. Mixtures of these metals may also be used. A specific example of a representative combustion promoter is platinum that is dispersed on an alumina support. If a solid combustion promoter is used, it can be prepared in a range of solid particle sizes or diameters, as appropriate for a given catalyst regeneration environment. For example, if regeneration of the second catalyst, as discussed above, occurs in a fluidized state, then the combustion promoter size is generally comparable to the second catalyst particle size and density so that the combustion promoter is fluidized together with the second catalyst.

The CO-containing regeneration flue gas stream is generally contacted with the second catalyst, all or a portion of which may also have coke deposited thereon, while it is being regenerated. In addition to the CO-containing regeneration flue gas stream, therefore, the second catalyst is also contacted with a second oxygen-containing regeneration gas stream. These streams may be mixed prior to introduction into a second regenerator containing the second catalyst, or may be introduced separately (e.g., to different locations of the second regenerator, depending on the residence time and average temperature of the CO-containing regeneration flue gas to obtain a desired degree of CO combustion without detrimentally affecting the second catalyst). For example, a CO-containing regeneration flue gas containing trace water may be fed to a catalyst cooler section of the second regenerator to cool this gas stream, possibly avoiding adverse hydrothermal consequences to the second catalyst. Contact between the regeneration flue gas and second catalyst may also be limited by feeding this gas stream to an upper dense bed section of the catalyst bed in the second regenerator, or even to a top section of the second regenerator that is above the upper dense bed section. Those skilled in art, in view of the present disclosure, will appreciate and be able to optimize the tradeoff between limiting exposure of the second catalyst to the CO-containing flue gas and obtaining complete CO combustion.

The second oxygen-containing regeneration gas stream may be the same as or different from the oxygen-containing regeneration gas stream used in the regeneration that provides the regeneration flue gas stream containing CO. The oxygen content of any oxygen-containing regeneration gas stream may be adjusted depending on the desired combustion temperature for a given regeneration, with higher oxygen contents directionally leading to higher temperatures and consequently an increased possibility for catalyst and/or equipment damage. Representative oxygen-containing regeneration gases are oxygen, oxygen comprising one or more inert diluents (e.g., nitrogen, argon, or helium), air, and air comprising one or more inert diluents, such as nitrogen-enriched air.

Regeneration in either regenerator is performed to remove at least a portion of the carbonaceous material or coke that deposits on catalyst (e.g., non-noble metal catalyst or second catalyst) during its normal use in a conversion process, thereby restoring the catalyst activity for the process before being returned to the reaction zone. A representative content of coke deposited on a catalyst, prior to removing it from a reaction zone and introducing it to a regenerator, will generally range from about 5% to about 25%, typically from about 8% to about 20%, and often from about 10% to about 15% by weight coke. Depending upon the particular catalyst and conversion process, it may be desirable to substantially remove the carbonaceous material, for example such that the regenerated catalyst comprises less than about 3%, or even less than about 1%, by weight coke, prior to being removed from the regenerator. In other cases, only partial regeneration may be sufficient, such that the regenerated the catalyst comprises from about 5% to about 10% by weight coke. Additionally, during regeneration there may be oxidation of sulfur and in some instances nitrogen compounds along with the removal of metals from the catalyst. Moreover, regeneration conditions can be varied depending upon the catalyst used and the type of contaminant material present upon the catalyst prior to its regeneration.

A non-limiting, representative process for regenerating a catalyst, according to a specific embodiment of the invention, can be illustrated with reference to FIG. 1. In particular, FIG. 1 depicts a catalytic process for converting an oxygenate (e.g., methanol) to light olefins, such as ethylene and propylene. This process is integrated with another catalytic process that further improves the yield of these light olefins, by cracking heavy olefin byproducts, such as $C_4$-$C_7$ olefins, of the methanol-to-light olefin conversion process.

As shown in FIG. 1, an oxygen-containing regeneration gas stream 10A (e.g., nitrogen-enriched air) is fed to a regenerator 101A containing a spent non-noble metal catalyst used in an olefin cracking process for converting, for example, $C_4$-$C_7$ olefins contained in a net feed stream 38B in an olefin cracking reactor 101B. At least a portion of the coke deposited on this non-noble metal catalyst is combusted in regenerator 101A and thereby removed from the non-noble metal catalyst as a result of its contact with oxygen in stream 101A. Incomplete combustion occurring in regenerator 101A results in the generation of a CO-containing flue gas stream 12A. The CO in stream 12A, however, is more completely combusted to $CO_2$ by feeding stream 12A, together with a second oxygen-containing gas stream 14 (e.g., air) to a second regenerator 102. Regenerator 102, unlike regenerator 101A, contains a combustion promoter comprising a noble metal (e.g., alumina having platinum deposited thereon), that is combined with a second catalyst. The presence of the noble metal on the combustion promoter in regenerator 102 provides a second regeneration flue gas stream 16 that is removed from regenerator 102 with complete or nearly complete removal of CO (e.g., in an amount of less than about 1% by volume in stream 16).

As illustrated in FIG. 1, the second catalyst may be regenerated continuously, for example in a fluidized bed in regenerator 102. The second catalyst, after regeneration to remove deposited coke to a desired level (e.g., less than about 3% by weight), is removed via transfer pipe 18 from regenerator 102 to reactor 103 comprising an oxygenate conversion reaction zone, which, in a particular embodiment, is for the conversion of methanol to light olefins such as ethylene and propylene. A feed stream 20 to this reactor 103 comprises methanol that is contacted with the regenerated second catalyst. Feed stream 20 is optionally added to the oxygenate conversion reaction zone together with a diluent stream 22 comprising, for example, steam. Other suitable diluents include helium, argon, nitrogen, carbon monoxide, carbon dioxide, hydrogen, paraffinic hydrocarbons, aromatic hydrocarbons (e.g., benzene and toluene). Mixtures of these diluents may also be used.

Representative conditions in the oxygenate conversion zone in reactor 103 include an absolute pressure from about 1 bar (15 psia) to about 10 bar (145 psia) and a temperature from about 300° C. (572° F.) to about 600° C. (1112° F.). The average residence time (e.g., based on the gas hourly space velocity (GHSV)) may be on the order of seconds to hours, as required to obtain desirable product yields (i.e., conversion and selectivity). Suitable catalysts for carrying out the desired conversion of oxygenates to light olefins include layered clays, zeolitic molecular sieves and non-zeolitic molecular sieves. Zeolitic molecular sieves in the calcined form may be represented by the general formula: $Me_{2/n}O:Al_2O_3:xSiO_2:yH_2O$ where Me is a cation, x has a value from about 2 to infinity, n is the cation valence and y has a value of from about 2 to 10. Known zeolites that may be used include chabazite (also referred to as Zeolite D), clinoptilolite, erionite, faujasite (also referred to as Zeolite X and Zeolite Y), ferrierite, mordenite, Zeolite A, Zeolite P, ZSM-5, ZSM-11, and MCM-22. Other zeolites include those having a high silica content, for example with silica/alumina ratios typically greater than 10, and often greater than 100. One such high silica zeolite is silicalite, as the term used herein includes both the silicapolymorph disclosed in U.S. Pat. No. 4,061,724 and also the F-silicate disclosed in U.S. Pat. No. 4,073,865, hereby incorporated by reference. Detailed descriptions of some of the above-identified zeolites are found in D. W. Breck, ZEOLITE MOLECULAR SIEVES, 1984, Robert E. Krieger Publishing Company, Florida.

Non-zeolitic molecular sieves include molecular sieves which have the proper effective pore size and are of the empirical chemical composition, on an anhydrous basis, expressed by the empirical formula: $(EL_xAl_yP_z)O_2$ where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01, and $x+y+z=1$. When EL is a mixture of metals, x represents the total amount of the element mixture present. Preferred elements (EL) are silicon, magnesium and cobalt, with silicon being especially preferred. These non-zeolitic molecular sieves are also referred to as "ELAPOs". The preparation of various ELAPOs are known in the art and described, for example, in U.S. Pat. No. 7,317,133, U.S. Pat. No. 5,191,141, U.S. Pat. No. 4,554,143, U.S. Pat. No. 4,440,871, U.S. Pat. No. 4,853,197, U.S. Pat. No. 4,793,984, U.S. Pat. No. 4,752,651, and U.S. Pat. No. 4,310,440.

The oxygenate conversion reaction zone in reactor 103 may be a fluidized bed of the catalyst described above. As the fluidized catalyst becomes spent by the deposition of coke (e.g., in an amount as described above), the spent (second) catalyst is transferred via transfer pipe 24 back to regenerator 102, thereby allowing for continuous reaction and regeneration. The oxygenate conversion effluent stream 26 from reactor 103, containing the light olefin reaction products as well as heavy olefin byproducts, is then fed to separation zone 104, which may comprise any number of single stage (e.g., flash) and/or multiple stage (e.g., distillation or fractionation column) separation vessels, as needed to separate components of oxygenate conversion effluent stream 26 with desired purities. As shown in FIG. 1, separation zone 104 is used to separate the components in oxygenate conversion effluent stream 26 to provide various purified streams, for example, fuel gas stream 28, ethylene product stream 30, propylene product stream 32, medium weight olefin stream 34 comprising butylene and other olefins (e.g., $C_4$-$C_7$ olefins as byproducts of the oxygenate conversion reaction), and heavy olefin stream 36, comprising $C_8$ and heavier hydrocarbons, including olefins. Under some operating conditions, this heavy olefin stream 36 comprises $C_6^+$ or $C_7^+$ olefins. Operating conditions may also be varied such that the medium weight olefin stream 34 comprises substantially all $C_4$-$C_6$ olefins or $C_4$-$C_5$ olefins.

At least a portion of the medium weight olefin stream 34 (e.g., a net stream 38B, comprising $C_4$-$C_7$ olefins, resulting from removal of purge stream 42) is passed to an olefin cracking zone in reactor 101B via net stream 38B. Conditions in reactor 101B are effective for the conversion or cracking of butylene and heavier olefins to provide additional amounts ethylene and propylene in olefin cracking effluent stream 40B, which are recovered in products streams 30 and 32 after being recycled to separation zone 104. The process conditions for olefin cracking are selected to disfavor hydrogen transfer reactions leading to the formation of paraffins, aromatics, and coke precursors. Favorable conditions therefore include a relatively high space velocity, low pressure, and high temperature.

Representative conditions maintained in the olefin cracking reaction zone of reactor 101B include a temperature from about 450° C. (842° F.) to about 600° C. (1112° F.), often from about 540° C. (1004° F.) to about 590° C. (1094° F.), and an absolute pressure from about 0.5 bar (7.3 psia) to about 10 bar (145 psia), often from about 1 bar (15 psia) to about 3 bar (44 psia). The liquid hourly space velocity (LHSV) typically ranges from about 5 to about 30 $hr^{-1}$, and often from about 10 to about 30 $hr^{-1}$. As is understood in the art, LHSV is the volumetric liquid flow rate over the catalyst bed divided by the bed volume and represents the equivalent number of catalyst bed volumes of liquid processed per hour. The LHSV is closely related to the inverse of the reactor residence time. The absolute olefin partial pressure generally ranges from about 0.1 bar (1.5 psia) to about 2 bar (29 psia), and typically from about 0.5 bar (7.3 psia) to about 1.5 bar (22 psia). A representative olefin partial pressure is atmospheric pressure. The olefin cracking reaction may be carried out in the presence of a diluent such as steam, nitrogen, methane, etc.

As shown in the representative flowscheme depicted in FIG. 1, the olefin cracking effluent stream 40B is recycled to the separation zone 104. However, the $C_4$ to $C_7$ olefins being recycled in streams 40B, 34, and 38B contain some paraffins, small amounts of which are formed in the olefin cracking reactor. It is therefore advisable to maintain a small purge stream 42 to avoid the excessive accumulation of the paraffins. This purge stream 42 may alternatively be removed from the stream 40B returning from the olefin cracking reactor 101B to the separation zone 104.

Representative catalysts useful in the olefin cracking reaction zone of reactor 101B comprise a crystalline silicate of the MFI family which may be a zeolite, a silicalite or any other silicate in that family or the MEL family which may be a zeolite or any other silicate in that family. Examples of MFI silicates are ZSM-5 and silicalite. An example of an MEL zeolite is ZSM-11 which is known in the art. Other examples are Boralite D and silicalite-2 as described by the International Zeolite Association (ATLAS OF ZEOLITE STRUCTURE TYPES, 1987, Butterworths). Preferred crystalline silicates have pores or channels defined by ten oxygen rings and a high silicon/aluminum atomic ratio.

Crystalline silicates are microporous crystalline inorganic polymers based on a framework of $XO_4$ tetrahydra linked to each other by sharing of oxygen ions, where X may be trivalent (e.g., Al, B, . . . ) or tetravalent (e.g., Ge, Si, . . . ). The crystal structure of a crystalline silicate is defined by the specific order in which a network of tetrahedral units are linked together. The size of the crystalline silicate pore openings is determined by the number of tetrahedral units (or, alternatively, oxygen atoms) required to form the pores, as well as the nature of the cations that are present in the pores. Crystalline silicates possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bi-directional intersecting pore system with the following pore diameters: a straight channel along [010]: 0.53-0.56 nanometers (nm) and a sinusoidal channel along [100]: 0.51-0.55 nm. Crystalline silicates with the MEL structure possess a bi-directional intersecting straight pore system with straight channels along [100] having pore diameters of 0.53-0.54 nm.

Crystalline silicates used in catalysts for olefin cracking may be formulated into bound pellets, spheres, extrudates, spray-dried powders, etc., as described in U.S. Pat. No. 7,317,133. Using a high silicon:aluminum ratio in the crystalline silicate catalyst, a stable olefin conversion can be achieved with a high propylene yield on an olefin basis of from about 20% to about 50%. The use of olefin cracking reactor 101B can therefore increase the total yield of ethylene and propylene in product streams 30 and 32 by as much as 10%, relative to the yield obtained from oxygenate conversion reactor 103 alone, due to the effective cracking of at least a portion of the byproducts (e.g., $C_4$-$C_7$ olefins) generated in the oxygenate conversion reaction zone of reactor 103.

After the olefin cracking catalyst in reactor 101B becomes sufficiently coked over the course of its use in the olefin cracking zone under the conditions discussed above, this catalyst, like the oxygenate conversion catalyst discussed above, is regenerated. The particular regeneration exemplified in FIG. 1 for the olefin cracking catalyst uses a swing-bed system with the appropriate piping and valves (not shown). This system allows net feed stream 38B to be diverted, using stream 38A, from reactor 101B to regenerator 101A, after the spent olefin cracking catalyst contained in this regenerator has been regenerated by contact with oxygen-containing regeneration gas stream 10A, as discussed above, to reduce the coke deposited on the catalyst, for example, to less than about 3% by weight. Likewise, when regenerator 101A is switched from its role as a regenerator to that of a reactor, the olefin cracking effluent stream is withdrawn from this vessel as stream 40A.

Spent catalyst, now in reactor 101B, is then regenerated by switching the role of this reactor 101B to that of a regenerator. Oxygen-containing regeneration gas is routed through stream 10B to this vessel and CO-containing flue gas is removed from it through stream 12B. In such a swing-bed regeneration operation, therefore, the catalyst beds may be physically stationary while the environment about the catalyst may be switched from a reaction to a regeneration environment. It is therefore apparent that, in the context of the present disclosure, "removing" a regenerated catalyst from a regenerator or "removing" a spent catalyst from a reactor does not necessarily require physical transfer of the catalyst.

Figure 2:
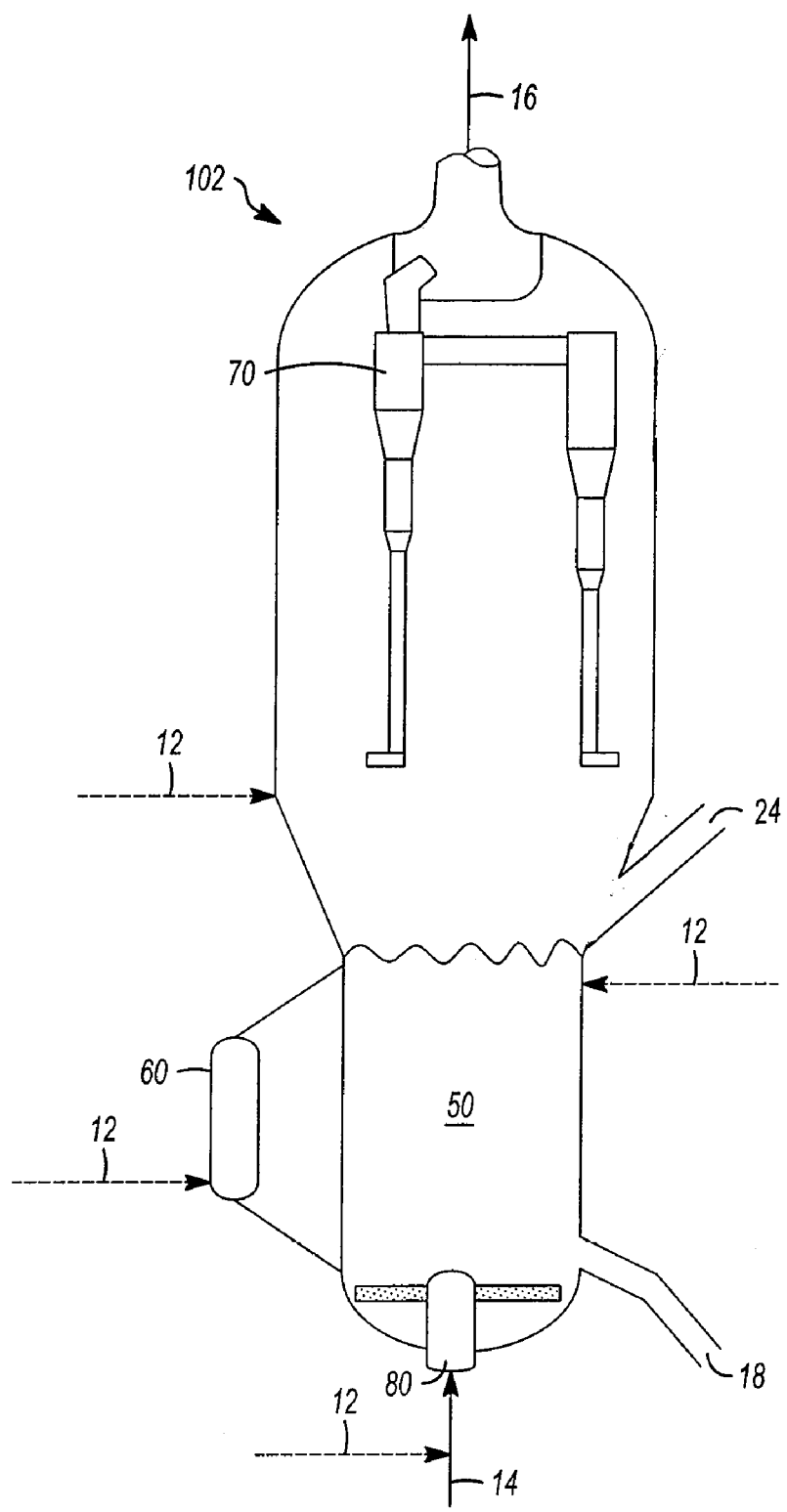
FIG. 2 depicts a representative regeneration section for a catalyst used in the oxygenate conversion process of FIG. 1.

FIG. 2 more closely illustrates the operation of regenerator 102 for regenerating the oxygenate conversion catalyst after it becomes spent due to coke deposition in reactor 103 of FIG. 1. Both reactor 103 and regenerator 102 may be operated continuously, for example in a fluidized manner to provide continual removal of (i) spent catalyst from reactor 103 to regenerator 102 through spent catalyst transfer pipe 24 and (ii) regenerated catalyst from regenerator 102 to reactor 103 through regenerated catalyst transfer pipe 18. As shown in FIG. 2, the second oxygen-containing gas stream 14 is fed to the bottom of regenerator 102, typically through a gas distributor 80. Other components of regenerator 102 include a catalyst cooler 60 that allows for heat removal from the regeneration process as well as cyclones 70 to improve the separation between the solid particles in regenerator 102, such as the oxygenate conversion catalyst and/or combustion promoter and the upwardly flowing second regeneration flue gas stream 16. Most of these solid particles reside in a dense bed 50.

While FIG. 1 shows the mixing of the CO-containing flue gas stream 12, resulting from the regeneration of the olefin cracking catalyst, with the second oxygen-containing gas stream 14 prior to entry to regenerator 102, FIG. 2 illustrates a number of alternatives. In particular, the CO-containing flue gas stream 12 may be added to regenerator 102 at a number of possible addition points, depending on the desired time and temperature of contact between stream 12 and the catalyst (and optionally combustion promoter) in regenerator 102. As discussed above, the optimal location will depend on a number of factors, including the hydrothermal stability of the particular oxygenate conversion catalyst system; the quantity, water content, and CO content of the CO-containing flue gas; and the regeneration temperature. Other suitable addition points for CO-containing flue gas stream 12 may include the catalyst cooler 60, an upper section of the dense bed 50, or a top section above the dense bed 50, with these alternatives shown in FIG. 2. With the knowledge gained from the present disclosure, those skilled in the art will be able to determine a location for introducing CO-containing flue gas stream 12 in a given regeneration system. The location may correspond to these or other addition points, or a combination of different addition points.

Overall, aspects of the invention are directed to integrated catalyst regeneration processes and particularly those comprising (i) combusting coke deposited on a catalyst in a regenerator that does not contain a noble metal to provide a regeneration flue gas stream comprising carbon monoxide and (ii) flowing the regeneration flue gas stream to a second catalyst in a second regenerator that does contain a noble metal. A regenerator "containing" a noble metal refers to the catalyst or and/or a combustion promoter within the regenerator that comprises a noble metal. Those having skill in the art, with the knowledge gained from the present disclosure, will recognize that various changes can be made in the above processes, as well as the corresponding flowschemes and apparatuses, without departing from the scope of the present disclosure. Mechanisms used to explain theoretical or observed phenomena or results, shall be interpreted as illustrative only and not limiting in any way the scope of the appended claims.

The invention claimed is:

1. A method for regenerating a catalyst having coke deposited thereon, the method comprising:
    (a) contacting an oxygen-containing regeneration gas stream with the catalyst to burn at least a portion of the coke and provide a regeneration flue gas stream comprising carbon monoxide (CO); and
    (b) contacting at least a portion of the regeneration flue gas stream with a second catalyst comprising a noble metal, or admixed with a combustion promoter comprising a noble metal, to combust at least a portion of the CO, wherein the second catalyst is in a second regenerator, wherein, during step (b), the second catalyst is regenerated by contact with a second oxygen-containing regeneration gas stream.

2. The method of claim 1, wherein the catalyst that is contacted with an oxygen-containing regeneration gas stream in step (a) does not comprise a noble metal and is not admixed with a catalyst comprising a noble metal.

3. The method of claim 1, wherein, during step (b), at least a portion of the second catalyst has coke deposited thereon.

4. The method of claim 1, wherein, in step (b), all of the regeneration flue gas stream is contacted with the second catalyst.

5. The method of claim 1, wherein the first oxygen-containing gas and the second oxygen-containing gas comprise air.

6. The method of claim 1, wherein the noble metal is platinum.

7. The method of claim 1, wherein the regeneration flue gas stream has a water content of less than about 1% by volume.

8. The method of claim 1, wherein step (b) provides a second regeneration flue gas stream comprising CO in an amount of less than about 1% by volume.

9. The method of claim 8, wherein the second catalyst is used in a fluidized bed process.

10. The method of claim 9, wherein the fluidized bed process is a fluid catalytic cracking (FCC) process or a process for converting an oxygenate to light olefins.

11. The method of claim 10, wherein the first catalyst is used in a process for cracking $C_4$-$C_7$ olefins to $C_2$ and $C_3$ olefins and the second catalyst is used in a process for converting methanol to $C_2$ and $C_3$ olefins.

12. An integrated process for regenerating a catalyst, the process comprising:
    (a) feeding an oxygen-containing regeneration gas stream to a regenerator containing a non-noble metal catalyst to burn at least a portion of coke deposited thereon;
    (b) removing a regeneration flue gas stream comprising carbon monoxide (CO) from the regenerator;
    (c) feeding (i) at least a portion of the regeneration flue gas stream and (ii) a second oxygen-containing regeneration gas stream to a second regenerator containing a second catalyst comprising a noble metal, or admixed with a combustion promoter comprising a noble metal, wherein the second catalyst or combustion promoter catalyzes combustion of at least a portion of the CO, wherein the non-noble metal catalyst and the second catalyst are not admixed; and
    (d) removing a second regeneration flue gas stream.

13. The process of claim 12, further comprising (e1) removing a regenerated non-noble metal catalyst, comprising less than about 3% by weight of deposited coke, from the regenerator.

14. The process of claim 13, further comprising, after step (e1), contacting the regenerated non-noble metal catalyst with a feed stream comprising $C_4$-$C_7$ olefins.

15. The process of claim 12, further comprising (e2) removing a regenerated second catalyst comprising less than about 3% by weight of deposited coke, from the regenerator.

16. The process of claim 15, further comprising, after step (e2), contacting the regenerated second catalyst with a feed stream comprising an oxygenate.

17. The process of claim 16, wherein the oxygenate is methanol.

18. The process of claim 12, further comprising:
removing a regenerated non-noble metal catalyst, comprising less than about 3% by weight of deposited coke, from the regenerator;
contacting the regenerated non-noble metal catalyst with a feed stream comprising $C_4$-$C_7$ olefins in an olefin cracking reaction zone;
removing a regenerated second catalyst comprising less than about 3% by weight of deposited coke, from the second regenerator;
contacting the regenerated second catalyst with a feed stream comprising methanol in a methanol conversion reaction zone,
wherein at least a portion of the $C_4$-$C_7$ olefins are generated in the methanol conversion reaction zone.

19. The process of claim 12, wherein step (c) comprises feeding at least a portion of the regeneration flue gas stream to a section of the second regenerator selected from the group consisting of a catalyst cooler section, an upper dense bed section, and a top section above the upper dense bed section.

20. An integrated catalyst regeneration process comprising:
combusting coke deposited on a catalyst in a regenerator, wherein the catalyst does not comprise a noble metal and is not admixed with a combustion promoter comprising a noble metal, to provide a regeneration flue gas stream comprising carbon monoxide; and
flowing the regeneration flue gas stream to a second catalyst in a second regenerator, wherein the second catalyst comprises a noble metal or is admixed with a combustion promoter comprising a noble metal, wherein the second regenerator is a separate vessel from the first regenerator, and the two catalysts are not mixed.

* * * * *